United States Patent [19]

Goymann et al.

[11] Patent Number: 4,978,357
[45] Date of Patent: Dec. 18, 1990

[54] ENDOPROSTHESIS

[75] Inventors: Volkmar Goymann, Essen; Emmanuel Anapliotis; Curt Kranz, both of Berlin, all of Fed. Rep. of Germany

[73] Assignee: MECRON medizinische Produkte GmbH, Berlin, Fed. Rep. of Germany

[21] Appl. No.: 204,819

[22] Filed: Jun. 10, 1988

[30] Foreign Application Priority Data

Jun. 12, 1987 [DE] Fed. Rep. of Germany ... 8708501[U]
Jan. 22, 1988 [DE] Fed. Rep. of Germany ....... 3802239

[51] Int. Cl.$^5$ ................................................. A61F 2/30
[52] U.S. Cl. ........................................ 623/18; 623/20; 623/23
[58] Field of Search ................. 623/16, 18, 20, 22, 623/23

[56] References Cited

U.S. PATENT DOCUMENTS 4,287,617 9/1981 Tornier ................................. 623/18

FOREIGN PATENT DOCUMENTS 0065481 5/1982 European Pat. Off. .
2356464 11/1973 Fed. Rep. of Germany .

Primary Examiner—David J. Isabella
Attorney, Agent, or Firm—Spencer & Frank

[57] ABSTRACT

An endoprosthesis is equipped with a collar and a prosthesis shaft and is adapted to be anchored longitudinally in a bone without the use of cement. A hip endoprosthesis can be constructed for anchorage in the proximal femur, in which the prosthesis shaft is composed of a plurality of parallel interconnected thin plates which are configured as plate-shaped partial faces and which have peripheral cutting edges which face away from the prosthesis collar. A tibial plateau prosthesis can be similary constructed, and includes a tibial plateau and a supporting structure formed of thin plates which extend in a common direction and which are interconnected. Both types of prosthesis can be driven into the bone without destruction of existing bone tissue and without removal of spongiosa. A shaft structure is employed which ensures the firmest possible anchorage in the medullary space, with a porous surface being provided to facilitate the in-growth of spongy material to thereby increase the strength of the anchorage of the prosthesis shaft.

7 Claims, 11 Drawing Sheets

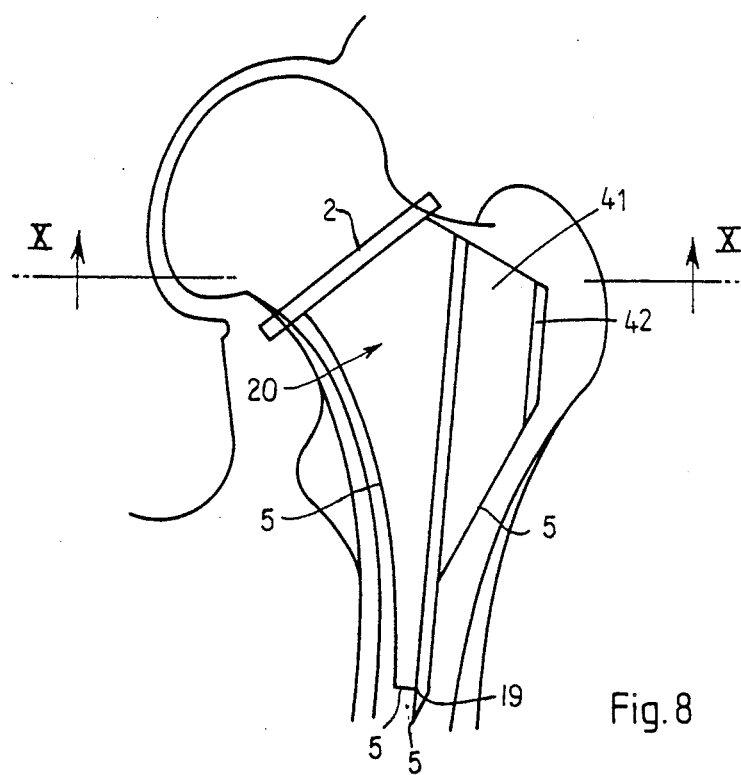
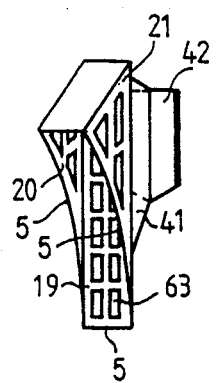
Fig. 9
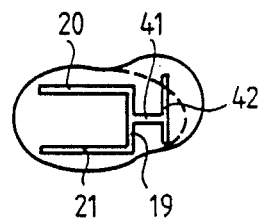
Fig. 10

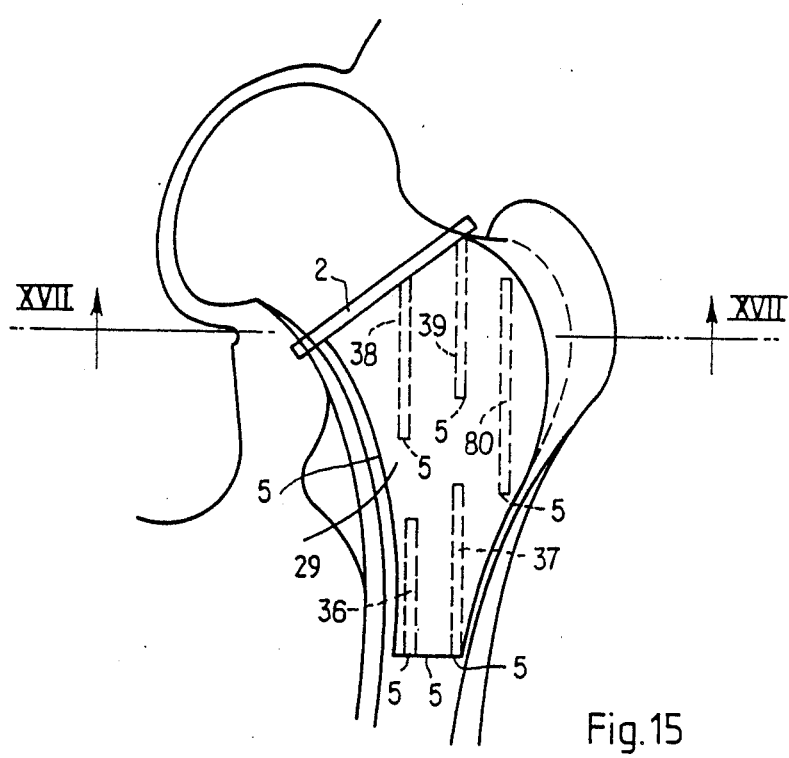
Fig. 15
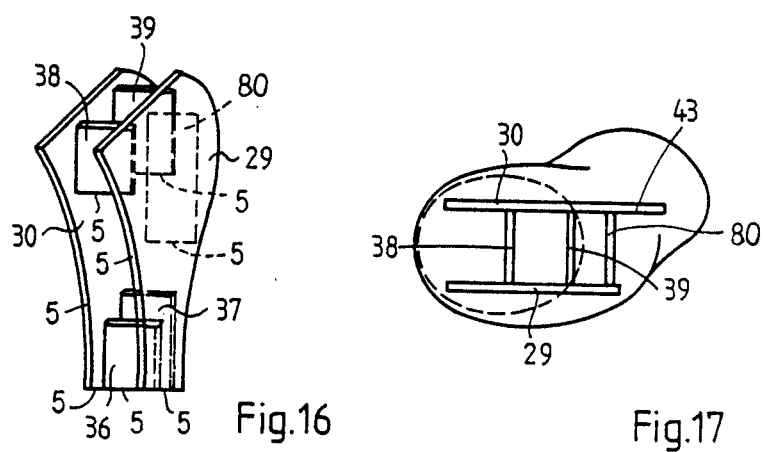
Fig. 16
Fig. 17

4,978,357

ENDOPROSTHESIS

BACKGROUND OF THE INVENTION

The present invention relates to an endoprosthesis and to a method of producing such an endoprosthesis.

Hip endoprostheses are known which are composed of a prosthesis head, a prosthesis collar and a prosthesis shaft which is anchored with the use of bone cement or without cement in the medullary space of the femur of a patient. If the prosthesis shaft is anchored in the medullary space without cement, a shaft structure is employed which ensures the firmest possible anchorage in the medullary space, with a porous surface being provided to facilitate the in-growth of spongy material to thereby increase the strength of the anchorage of the prosthesis shaft.

However, the anchorage of the prosthesis shaft in the medullary space of the femur requires substantial removal of spongiosa from the intertrochantic region. Yet, the removal of spongiosa must be considered as a non-physiological local interference in the sense of defect formation since it adversely affects stress adaptation capabilities as well as primarily age-specific adaptation capabilities.

A further drawback of the prior art endoprosthesis is the irregular force distribution due to a primarily distal introduction of the forces into part of the thigh which is distal to the intertrochantic region, thus taking the bone portion intended for this purpose out of the functional load. This results in atrophy rather than in the desirable functional stimulation of the bone to cause it to grow onto the endoprosthesis in a fixing manner.

The consequence of both these drawbacks is premature loosening of the endoprosthesis and the resulting necessity of revisionary or corrective surgery. However, considerable difficulties are encountered in such revisionary or corrective surgery in connection with many types of endoprostheses because many of the respective prosthesis shafts are configured in such a way that removal of the endoprosthesis is possible only with considerable destruction of the bone material, which ultimately makes the growing-in of a new endoprosthesis more difficult and sometimes impossible.

A further drawback of prior art endoprosthesis is that standard models exist for different femur sizes, but these standard models are not adapted to the individual shape of the proximal femur of a patient. This causes any unfavorable force introduction in many endoprosthesis to be augmented, and therefore the existing bone substance is not utilized in an optimum manner.

Finally, the prior art endoprostheses require costly surgical techniques in which it is necessary to preliminarily chisel or drill the bone which is to receive the prosthesis so as to enable it to receive the prosthesis shaft. This must be done with the utmost of caution since it is necessary to avoid unnecessary damage to the bone structure as well as to avoid making a hole that is so large that the prosthesis shaft cannot be anchored with sufficient strength. Moreover, a considerable amount of time is required to rasp or drill open the bone, which considerably increases the risk of infection. Also, in these prior art devices it is necessary to open the medullary channel, thereby raising a considerable danger of bone destruction due to a via falsa, i.e. an incorrect channel opening which must be re-drilled.

A tibial plateau prosthesis is disclosed in German Offenlegungschrift (German unexamined patent application) No. 3,429,157 as a tibial plateau implant that is implanted without cement and is composed of a metal plate and a plastic slide bearing fastened thereon. It includes an insertion plate which is fastened to the metal plate on a side which is facing away from the slide bearing, the insertion plate being disposed essentially perpendicularly to the metal plate. In the prior art prosthesis, the insertion plate serves essentially to prevent tilting and/or displacement of the tibial plateau in spite of the cementless implantation when the knee joint is in a stressed bent position. To produce a firm connection between a tibial plateau and a tibia head, a bone screw is screwed through the insertion plate into the head of the tibia which, however, results in a more difficult attachment of the tibial plateau and, moreover, introduces additional stress on the tibia.

It is a problem in the art to provide a tibial plateau prosthesis which can be easily attached and connected with the tibia in a manner secure against displacement as well as tilting.

SUMMARY OF THE INVENTION

It is an object of the present invention to provide an endoprosthesis of the above-mentioned type which ensures the retention of the physiology of the medullary space in the bone inclusive of the intertrochantic spongiosa. This provides favorable anatomical conditions for revisionary surgery, great potential for adaptation to age-specific bone changes, simplified surgical techniques without the necessity of preliminary chiseling or drilling, and optimum physiological force introduction, while providing an enlarged contact surface for the in-growth of bone material, thereby permitting individual adaptation to the shape of patient's femur.

The above and other objects are accomplished according to the invention by the provision of a prosthesis including:
  a collar;
  a prosthesis shaft supporting said collar and being adapted to be anchored longitudinally in a bone without the use of cement;
  the prosthesis shaft being composed of a plurality of plates; the plurality of plates extending generally in a common longitudinal direction;
  each of the plurality of plates being connected to at least one other one of the plurality of plates; each of the plurality of plates respectively having a peripheral edge which is adapted for cutting into bone.

The solution according to the present invention permits the application of an endoprosthesis while retaining the spongy structures of the bone so that the biometabolism of the patient is not interfered with and blood circulation conditions are not substantially changed. By retaining the physiology of the medullary space of the bone including the intertrochantic spongiosa, favorable anatomic conditions are created for revisionary surgery, and optimum adaptation conditions are created for aging-specific bone changes. The endoprostheses according to the present invention permit reliable anchoring by use therein of a plurality of thin plates, each provided with a peripheral cutting edge. These prostheses each can include plurality of respective thin, graduated plates, which are to be driven into a bone, the plates being self-cutting due to their sharp edges, and therefore require no pre-cutting or rasping. A significant prerequisite for the driving-in of a prosthesis shaft is that all partial faces of the endoprosthesis system to be driven in are disposed so as to extend in a single direction and must be driven in a direction parallel to the axis of the femur, i.e. perpendicular to its cross section, without requiring additional preparatory work.

Such a procedure offers substantial surgical advantages since rasping or drilling open of the bone is not required, resulting in a considerable saving of time, a reduction of the risk of infection, and the avoidance of a via falsa.

Since the number and cross-sectional configuration of the plurality of thin plates can be selected at random, it is possible on the one hand to have a large contact surface for the in-growth of bone material and, on the other hand, to create with relatively inexpensive means the prerequisite of individual adaptability of the endoprosthesis to the respective bone shape.

According to the invention, a coarsely permeable foreign body is introduced as a fixing member, with the spongiosa of the bone being cut apart only once during the driving-in process so that the plurality of plates can then be adapted accurately to the cut surface over a major portion of it.

The application of a prosthesis to the femur of a patient made possible by the configuration of the endoprosthesis according to the invention with optimum protection of the spongiosa creates a secure physiological fit, with the spongy structures offering an extremely firm hold and permitting the transfer of relatively large pressure forces.

The intertrochantic laminar prosthesis according to the invention permits a secure seat by providing for planar contact of a prosthesis collar on the cortical substance of the resection incision at the neck of the limb and the spongy structure present there. It is not significant in this regard whether a horizontal or oblique incision is selected by the surgeon.

According to other advantageous features of the invention a plurality of laminae, and/or the connecting laminae, and/or the extension webs or extending angles, are provided with bores and/or perforations. This creates additional free spaces for the in-growth of spongy material so that, on the one hand, the complex meshed structure of the spongiosa is utilized to transfer the occurring forces and, on the other hand, an optimum connection of the endoprosthesis with the bone is ensured, so that loosening of the endoprosthesis is only slightly likely to be encountered.

In a method for producing an endoprosthesis of the above-mentioned type, ventral and dorsal plates are cut according to an X-ray template produced from the bone of a patient. A plurality of individual partial faces are individually adapted to the shape of the neck of the femur or to the shape of the ridge of the trochanter, respectively, and are then assembled. This results in an excellent adaptation of the endoprosthesis to the respective shape of the bone, and thereby results in a highly favorable introduction of forces with secure seating in the bone with an optimum utilization of the available bone material.

Another advantageous embodiment of the invention relates to a prosthesis of the above-mentioned type in the form of a tibial plateau prosthesis.

In this embodiment, it is possible to attach a tibial plateau in the dorsal-ventral direction of the bone and to ensure that the tibial plateau is fastened in a secure manner against displacement and tilting. Since the tibial plateau prosthesis in this embodiment is set in ventrally and is driven into the tibia in the dorsal direction, it is only necessary to laterally change the position of the frontal knee joint ligaments. The large areas formed by the plates in the transverse direction prevent tilting of the tibial plateau even under the stress of a bent knee and the action of a bending moment acting on the prosthesis connected therewith, which in the prior art tibial plateaus resulted in the tibial plateau coming loose from its anterior connection with the bone seat due to the tensile stresses acting on the anterior region of the plateau.

In an advantageous embodiment, the lower edges of the plates facing the tibial plateau ar connected with one another by means of one or more connecting webs, or by a first connecting plate, so that the plates form a U-shaped or dove-tailed fastening element with the connecting plate. According to this embodiment of the invention, the stability of the attachment of the tibial plateau is increased, thereby increasing the security thereof against displacement or tilting of the tibial plateau.

In a further advantageous embodiment, the front edges of the plates facing the tibial plateau and of the connecting plate, respectively, are given a cutting edge which facilitates driving of the fastening element into the tibia and results in minimal damage of the tibia.

Additional perforations provided in the plates and in the connecting plates permit the growth of bone tissue through the perforations to thereby provide supplemental stabilization of the tibial plateau.

The invention will be described in greater detail below with reference to embodiments of the invention which are illustrated in the drawings.

BRIEF DESCRIPTION OF THE DRAWINGS

FIG. 8 is a schematic side elevational view of a fourth embodiment of an intertrochantic laminar prosthesis mounted on a femur.

FIG. 9 is a perspective view of the prosthesis of FIG. 8.

FIG. 10 is a schematic sectional view taken along line X—X of FIG. 8.

FIG. 15 is a schematic side elevational view of a seventh embodiment of an intertrochantic laminar prosthesis.

FIG. 16 is a perspective view of the prosthesis of FIG. 15.

FIG. 17 is a schematic cross-sectional view as taken along line XVII—XVII of FIG. 15.

DETAILED DESCRIPTION OF THE PREFERRED EMBODIMENTS

Figure 1:
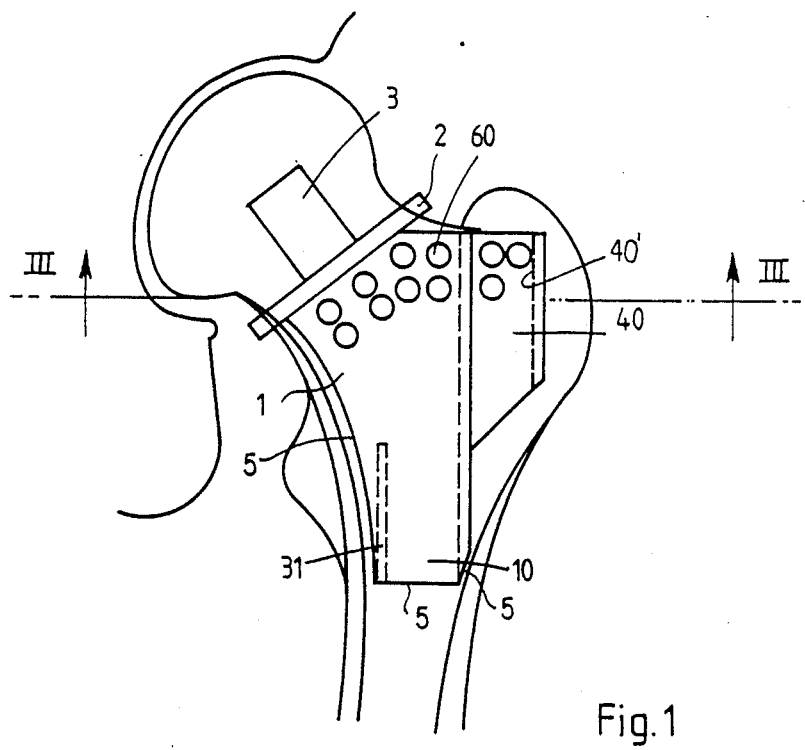
FIG. 1 is a schematic side view of an intertrochantic laminar prosthesis mounted on a femur, according to a first preferred embodiment of the invention.
Figure 2:
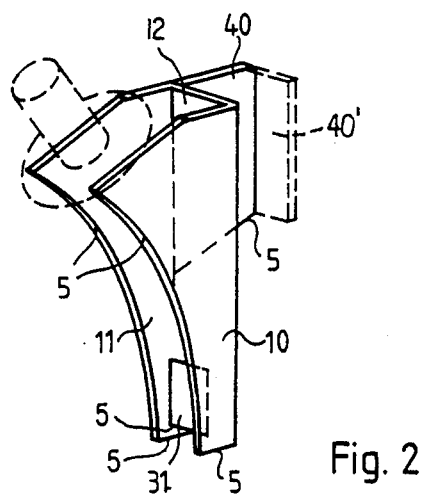
FIG. 2 is a perspective view of the prosthesis of FIG. 1.
Figure 3:
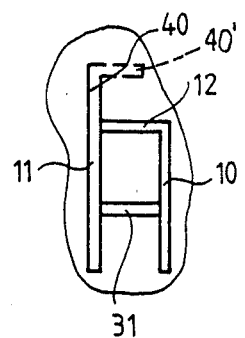
FIG. 3 is a schematic cross-sectional view of the prosthesis mounted in the femur, taken along line III—III of FIG. 1.

FIGS. 1 to 3 are respectively a side view, a perspective view, and a cross-sectional view of an intertrochantic laminar prosthesis, with the side view of FIG. 1 including a schematic representation of a femur to indicate the position of the endoprosthesis and its configuration which is adapted to the shape of the bone.

The laminar prosthesis is composed of a prosthesis shaft 1, a prosthesis collar 2 and a cylindrical pin 3 to receive a prosthesis head (not shown). The prosthesis shaft 1 includes two thin plates 10 and 11 which are connected by a plate 12, plates 10 and 11 being disposed parallel to one another and being configured in the form of plate-shaped partial faces whose peripheral edges are configured as cutting edges 5. One of the cutting edges 5 of the plates 10 and 11 is arcuate and conforms to the exterior shape of the femur. The upper end of the prosthesis shaft 1 (as viewed in FIG. 1) is hereafter referred to as the proximal end, and the lower end of the prosthesis shaft 1 is referred to hereafter a the distal end, this terminology being used with reference to the joint which is formed by installation of the prosthesis. The terms ventral and dorsal refer respectively to the front and back of the body.

The plate 11 is connected with an extension web 40 (shown in solid outline in FIGS. 1 to 3) or with an angle 40' (shown in dotted outline in FIGS. 1 to 3), which may be formed in one piece. The extension web 40 or angle 40' (whichever is used) is also provided with a lower cutting edge 5. The two mutually parallel thin plates 10 and 11 are also connected with one another by a thin connecting plate 31 whose underside is also provided with a cutting edge 5. The thin plates 10, 11, and 12, and the extension web 40 or the angle 40' (whichever is used), are provided with a plurality of bores 60 into which spongy material of the bone is able to grow.

The laminar prosthesis shown in FIGS. 1 to 3 has a U-shaped cross section (formed by plates 10, 11, and 12) and a large surface area (having bores therethrough or recesses therein) for the attachment and in-growth of spongy material. The laminar prosthesis of the present invention has a highly advantageous shape which is adapted to conform closely to the shape of the bone as seen in side view in FIG. 1. Due to the fact that the thin plates 10, 11, and 12 extend in a parallel direction to the longitudinal direction of the prosthesis shaft 1 and due also to the fact that the connecting plate 31 and the extension web 40 or the angle 40' (whichever is used) also extend in a parallel direction to the longitudinal direction of the prosthesis shaft 1, the laminar prosthesis can be inserted or driven in perpendicularly to the longitudinal axis of the femur without the necessity of prior chiseling or drilling.

Due to the provision of the cutting edges 5, the driving in of the intertrochantic laminar prosthesis is facilitated. In this way, the normal physiology of the bone is fully retained and, if revisionary surgery should become necessary, there still is available sufficient bone substance. Due to the parallel extending partial faces, e.g. those faces having the cutting edges 5, the resection of the endoprosthesis during such a revisionary operation can be performed without significant damage to the bone.

The open structure of the endoprosthesis shown in FIGS. 1 to 3 creates the proper conditions for the spongiosa to grow all about and within the prosthesis, which prevents the prosthesis from becoming loose even under heavy and changing stresses.

The laminar (plate-like) structure of the prosthesis permits, by relatively simple means, individual adaptation of the prosthesis to conform relatively closely to the respective anatomy of the bone. Since only the plate-shaped partial faces (having the cutting edges 5) require machining, milling, or other processing steps, the laminar structure of the prosthesis also creates the proper conditions to facilitate shaping the thin plates (e.g. plates 10 and 11), and/or the connecting plates (e.g. 12 and 31), and/or the extension web or angle (e.g. 40 and 40', respectively) in such a manner that, with respect to the anatomy of the respective bone, a highly favorable force introduction and a relatively uniform force distribution can take place without pressure concentrations.

By the additional use of a microporous biocompatible material for the thin plates 10, 11, and 12 the connecting plate 31, and the extension web 40 (or the angle 40'), the surface structure of the prosthesis can be further improved so that the strength of the seat of the endoprosthesis in the bone is augmented.

Figure 4:
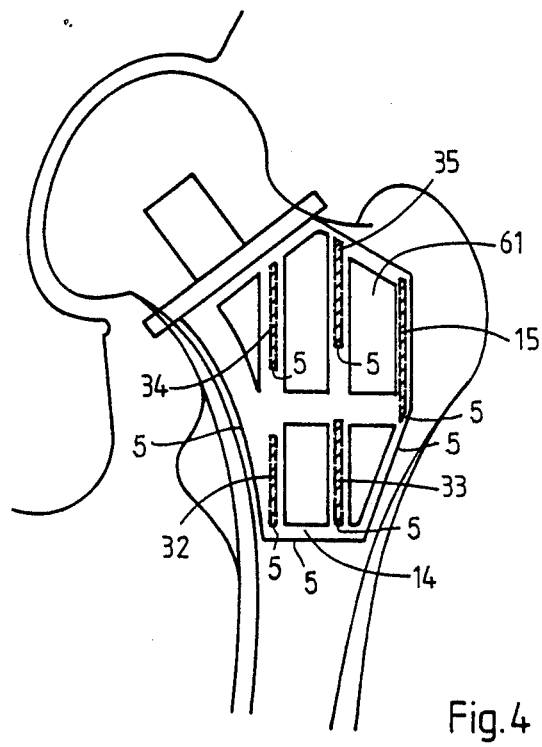
FIG. 4 is a schematic side view of a second embodiment of an intertrochantic laminar prosthesis mounted on a femur.
Figure 5:
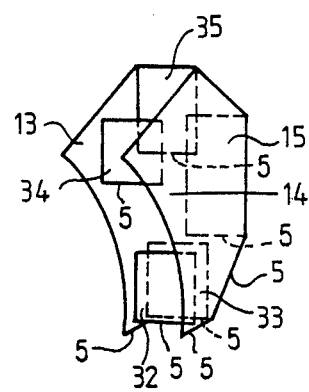
FIG. 5 is a perspective view of the prosthesis of FIG. 4.

FIGS. 4 and 5 show a variation of the intertrochantic laminar prosthesis which is composed of two parallel primary plates 13 and 14, and a plate 15 which connects the parallel primary plates 13 and 14. In addition, the two primary plates 13 and 14 are connected with one another by means of connecting plates 32 to 35 which contribute to an enlarged surface area. Here again, the thin plates are provided with peripheral cutting edges 5. The primary plates 13, 14 and 15, and also possibly the connecting plates 32 to 35, are preferably provided with perforations 61 which permit spongy bone material to grow therethrough.

As can be seen particularly in the side view of FIG. 4, this shape of the prosthesis is optimally adapted to conform to the shape of the bone so that a maximum of the available bone surface area is being utilized.

Figure 6:
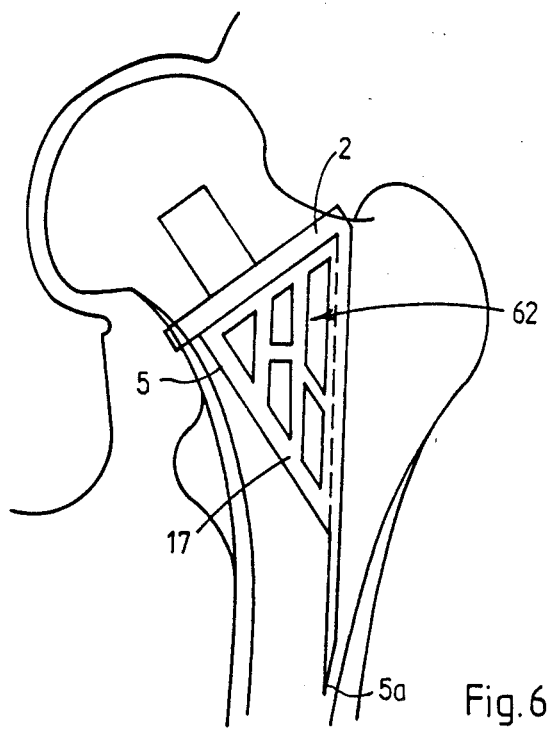
FIG. 6 is a schematic side elevational view of a third embodiment of an intertrochantic laminar prosthesis.
Figure 7:
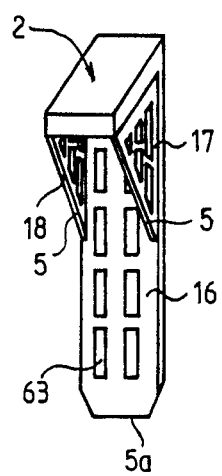
FIG. 7 is a perspective view of the prosthesis of , FIG. 6.

FIGS. 6 and 7 show an intertrochantic laminar prosthesis including a plate-shaped primary lamina 16, hereafter referred to as primary plate 16, which is connected with the prosthesis collar by two triangular lateral plates 17 and 18. A distal end 16a (the lowermost end in FIG. 7) of the primary plate 16 is tapered so that the primary plate 16 is in the shape of a trapezoid. The primary plate 16 has perforations 63 which, in this embodiment, each have a rectangular shape. The perforations 62 provided in the triangular side plates 17 and 18 are adapted in shape to the outer perimeter shape of the lateral plates 17 and 18, as seen in FIG. 6. These perforations 62 cause the plates 16, 17, and 18 to each have a grid-like structure. The lower cutting edge 5a of the primary plate 16 permits easy driving of the intertrochantic laminar prosthesis into the femur.

FIGS. 8 to 10 show a further variation of an intertrochantic laminar prosthesis similar to FIGS. 6 and 7.

This prosthesis is composed of a primary plate 19 provided with perforations 63 and laterally attached lateral plates 20 and 21 whose peripheral cutting edges 5 have an arcuate shape to adapt them to conform to the shape of the bone. In addition, an extension web 41 is attached to the center of the primary plate 19 and is connected at a right angle with an extension plate 42 so that a T-shaped extension is produced.

Figure 11:
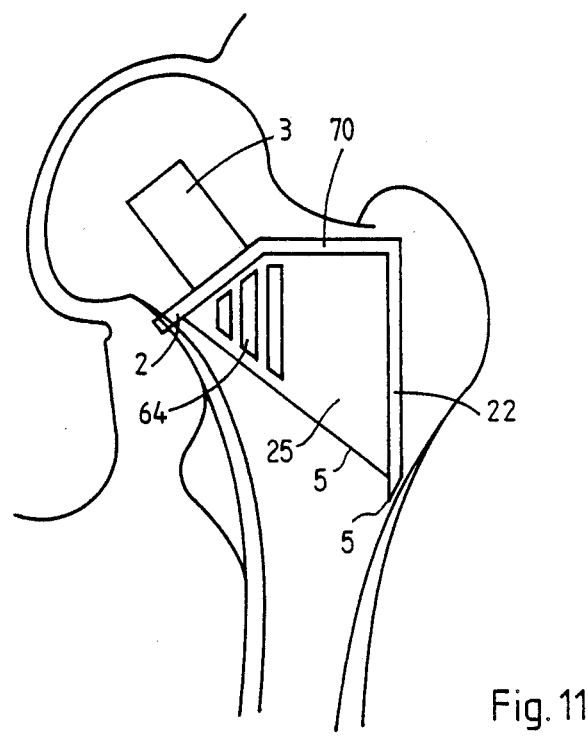
FIG. 11 is a schematic side elevational view of a fifth embodiment of an intertrochantic laminar prosthesis.
Figure 12:
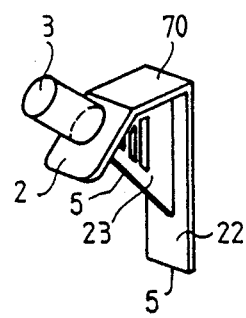
FIG. 12 is perspective view of the prosthesis of FIG. 11.

FIGS. 11 and 12 are respectively a side view and a perspective view of an intertrochantic laminar prosthesis including a primary plate 22 which is connected at an approximately right angle with an upper cover face 70 followed by prosthesis collar 2 and the cylindrical pin 3 which is adapted to receive the prosthesis head. In the center of the primary plate 22, there is attached a thin plate 23 whose outer edges are connected with the cover face 70 and with the prosthesis collar 2. The lower peripheral edge of the thin plate 23 is given a cutting edge 5 similar to that of the lower edge of the primary plate 22.

Figure 13:
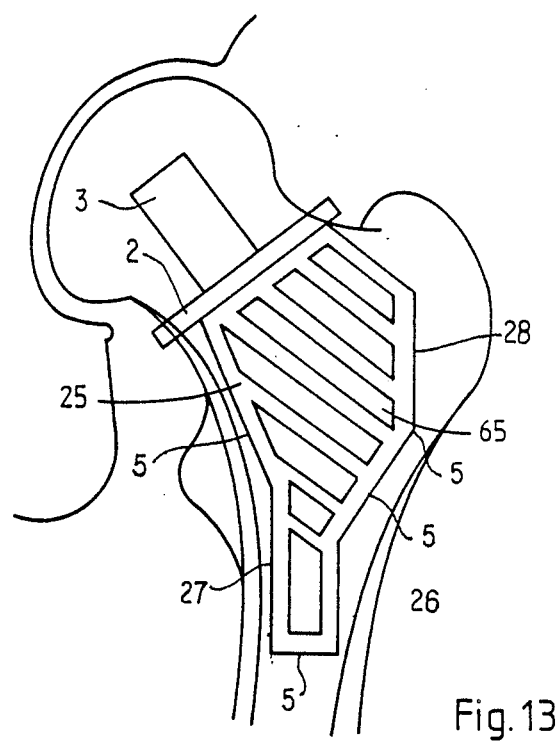
FIG. 13 is a schematic side elevational view of a sixth embodiment of an intertrochantic laminar prosthesis.
Figure 14:
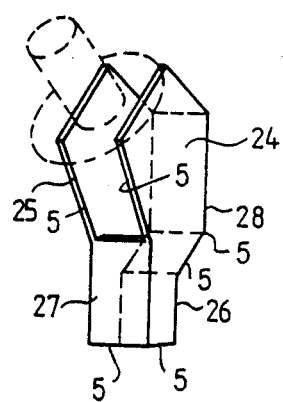
FIG. 14 is a perspective view of the prosthesis of FIG. 13.

FIGS. 13 and 14 are a side view and a perspective view, respectively, of a box or funnel shaped intertrochantic laminar prosthesis. It is composed of thin, mutually parallel plates 24 and 25 and of thin plates 26, 27 and 28 which are oriented parallel to the longitudinal direction of the prosthesis shaft and interconnect with the two thin plates 24 and 25. In this embodiment as well, the respective peripheral edges of the plates 24 to 28 are configured as cutting edges 5 and are provided with a plurality of perforations 65 which are adapted to conform in shape with the external geometry of the thin plates 24 to 28.

FIGS. 15 to 17 are respectively a side view, a perspective view and a cross-sectional view of a box or funnel-shaped intertrochantic laminar prosthesis composed of two parallel extending ventral and dorsal plates 29 and 30. Connecting plates 36 to 39 are disposed between and interconnecting the two plates 29 and 30. As can be seen in the cross-sectional view of FIG. 17, one thin plate 30 has an extended web 43 which, in the implanted state of the prosthesis, is disposed in the major trochanter. In this embodiment as well, the respective lower peripheral edges of each of the plates described above are configured as cutting edges 5. A plurality of perforations (not shown) can be provided in these plates, and these perforations can be adapted to conform in shape with the external perimeter geometry of the thin plates.

FIGS. 18 to 22 show intertrochantic laminar prostheses having a closed contour when seen in cross section, with both views representing only a single selection from a very large number of possible closed contours. These figures are discussed hereunder.

Figure 18:
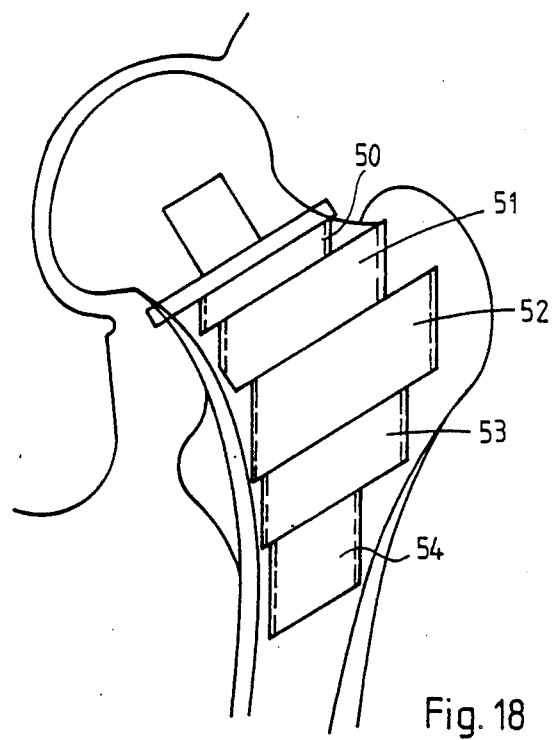
FIG. 18 is a schematic side elevational view of an eighth embodiment of an intertrochantic laminar prosthesis.
Figure 19:
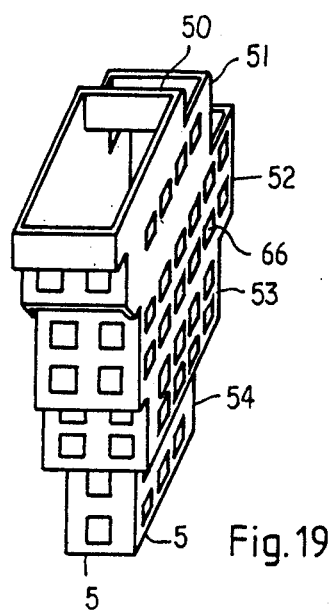
FIG. 19 is a perspective view of the prosthesis of FIG. 18.
Figure 20:
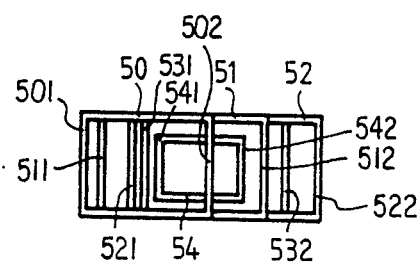
FIG. 20 is a schematic top elevational view of the prosthesis of FIG. 18 with the prosthesis collar and the conical pin removed for clarity.

FIGS. 18 to 20 show a box-shaped, stepped intertrochantic laminar prosthesis in which the individual thin plates have a closed rectangular structure when seen in cross section, and the individual elements 50 to 54 are connected with one another in a manner offset to one another and adapted to conform to the external contour of the bone. The plates 54, 57 are respectively connected to the walls of the adjacent element 53 by any type of connection means, such as by a plurality of struts 555, as seen in FIG. 20. The respectively projecting lower peripheral edges are configured as cutting edges 5. In addition, the elements 50 to 54 are provided with a plurality of perforations 66 which permit ingrowth of spongiosa.

Figure 21:
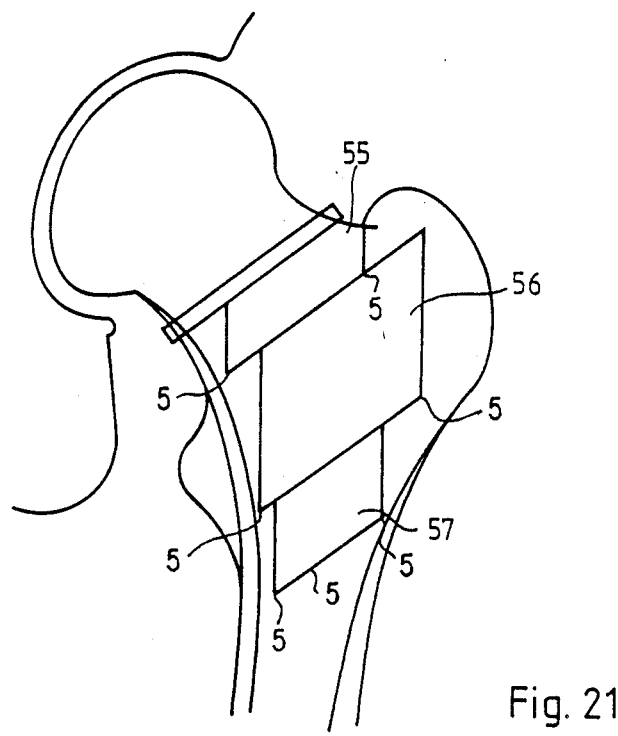
FIG. 21 is a schematic side elevational view of a ninth embodiment of an intertrochantic laminar prosthesis.
Figure 22:
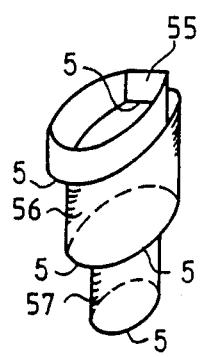
FIG. 22 is a perspective view of the prosthesis of FIG. 21.

FIGS. 21 and 22 show an embodiment which is similar to that of FIGS. 18 to 20 wherein a closed laminar structure has a plurality of individual thin plates which each have an arcuate, closed contour and are connected with one another in a manner adapted to conform to the external shape of the bone. In this embodiment as well, the lower projecting edges are configured as cutting edges 5.

Figure 23:
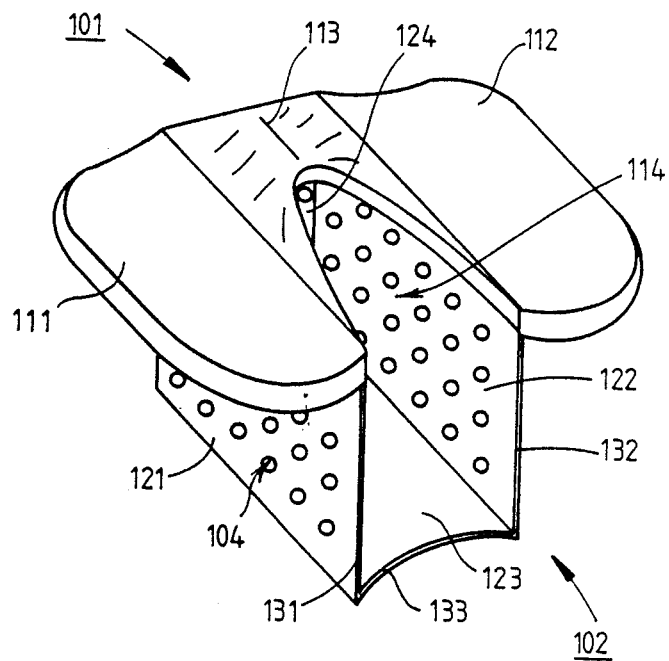
FIG. 23 is a schematic perspective view of a tibial plateau prosthesis according to the invention.

FIG. 23 is a perspective view of the tibial plateau prosthesis according to the invention which includes a tibial plateau 101 provided at its upper side with two supporting faces or joint sockets 111, 112 corresponding to the condyles of the femur with a curvature which is concave in the ventral-dorsal direction. A center web 113 as well as a recess 114 in the plateau are provided between the joint sockets 111 and 112.

At the underside of tibial plateau 101, i.e. on the side of the tibia, there are provided two parallel plates 121 and 122 in a dorsal-ventral orientation. The spacing between these plates approximately corresponds to the Widest point in the recess 114 of the tibial plateau. The lower edges of the two parallel plates 121 and 122, i.e. the edges opposite the tibial plateau 101, are connected together by means of a first connecting plate 123. A second connecting plate 124 connects the rear edges of the two plates 121 and 122, as well as the rear edge of the first connecting plate 123. By analogy to the description of FIG. 1, the plates 121, 122, 123 can be referred to as a 'shaft' of the tibial plateau 101.

The front edges 131, 132 and 133 of the plates 121, 122 and of the first connecting plate 23 are configured as cutting edges 5 and are sharp edges, in order to facilitate the driving of the tibial plateau prosthesis into the head of the tibia. For better guidance and to further facilitate the driving in of the prosthesis, the front edge 133 of first connecting plate 123 is given an undercut in the shape of a circle segment.

The parallel plates 121 and 122, and also if desired the connecting plates 23 and 24, are provided with a plurality of perforations 104 which serve to permit the ingrowth of bone tissue after implantation of the tibial plateau prosthesis to thereby increase the service life and stability of the tibial plateau prosthesis.

A variation is contemplated from the embodiment shown in FIG. 23, wherein the U-shaped fastening element 102 (which is formed by the plates 121, 122 and the connecting plates 123, 124) may also be configured as a dove-tail fastening element 102, with the plates 121, 122 preferably being inclined progressively outwardly in the direction away from the joint sockets 111 and 112. It is also possible in this variation to omit the connecting elements 123 and 124 if it is ensured that the plates 121 and 122 have sufficient stability.

The operation and attachment of the tibial plateau prosthesis according to the invention will be described in greater detail below with reference to FIGS. 24 and 25.

Figure 24:
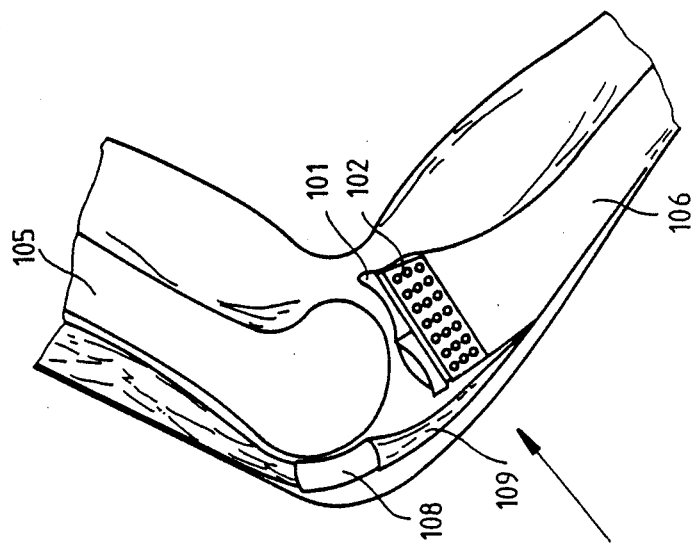
FIG. 24 is a schematic side view of a knee joint with the intertrochantic laminar prosthesis of FIG. 23 fastened to the head of the tibia.

FIG. 24 is a schematic side view taken along a midsection of a knee joint. FIG. 24 schematically shows a femur 105, a tibia 106, a patella 108 and a schematic-sectional view of the anterior crucial ligaments 109. After exposing the joint and removing the cartilaginous areas of the tibial plateau medially and laterally, the tibial plateau prosthesis 101, 102 (shown schematically in section in FIG. 24) is driven into the head of the tibia in the direction of the arrow shown in FIG. 24. The prosthesis takes along with it a narrow spongy subchondral bone lamina (not shown), with the cutting edge shaped anterior edges 131 to 133 of the plates 121 and 122, and of the first connecting plate 123, facilitating the driving in of the prosthesis. In the resultant final position of the tibial plateau prosthesis shown in FIG. 24, an upper slide face of the tibial plateau, which is preferably made of polyethylene, is oriented toward the femur condyles which, in the case of a total endoprosthesis, are also an implant, while for a partial endoprosthesis, the natural femur condyles are still present.

As can be seen in the side view of the knee joint of FIG. 24, in this position of the tibial plateau prosthesis the anterior crucial ligaments 109 additionally secure the prosthesis due to their firm contact at the head of the tibia 106. These ligaments 109 thereby prevent any outward displacement of the prosthesis in the dorsal-ventral direction when the knee is bent considerably while the second connecting plate 124 prevents displacement in the ventral-dorsal direction.

Figure 25:
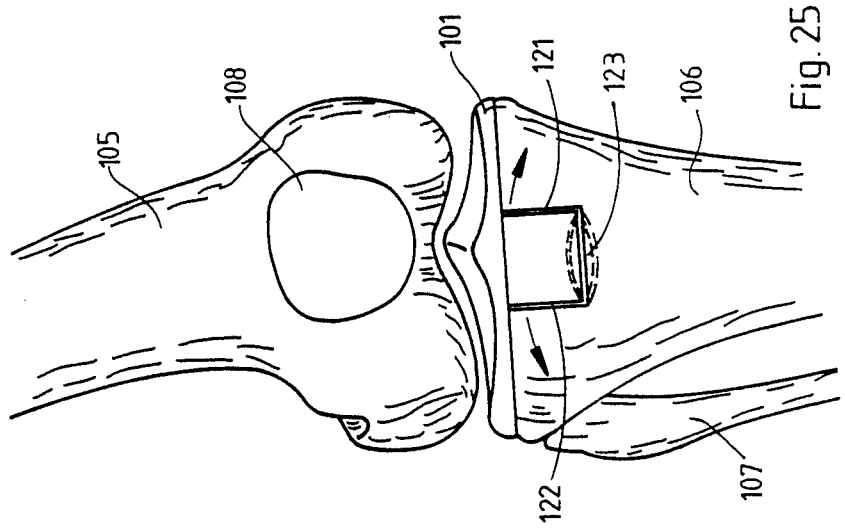
FIG. 25 is a schematic top view of a knee joint with the prosthesis of FIG. 23 fastened to the head of the tibia.

The front view of the knee joint of FIG. 24 shown in FIG. 25 shows the femur 105, the tibia 106, the patella 108, the fibula 107 and the tibial plateau prosthesis fastened in the head of the tibia 106. From this view it is clear how the large areas formed by the plates 121, 122 in the transverse direction prevent tilting away of the prosthesis in the two directions shown by the unnumbered arrows in this figure. The connecting plate 123 which is shown in FIG. 25 as a planar plate, may selectively also have a convex or concave shape as shown by the two positions indicated in dashed outline in this figure.

The above-described intertrochantic laminar prostheses are distinguished by the fact that the transfer and transmission of pressure forces into the femur takes place proximally from the head of the hip joint and its spongiosa and from the spongy and cortical components of the neck of the femur. Thus the physiology of the medullary space including the intertrochantic spongiosa is retained during the introduction of the prosthesis, so that biological adaptation in the course of aging is possible. In prior art prosthesis types, the pressure force at the calcar femoral (i.e., the femoral spur) is reduced by 60%, which leads to radiologically detectable resorption. In contrast, in the above-described laminar prosthesis, the forces are introduced physiologically, thereby ensuring a secure seat of the prostheses at the neck of the femur and very good anchorage in the proximal femur.

The assembly of the prostheses according to the invention from individual plates makes it possible to easily consider and construct any configuration of a prosthesis which is adapted to the neck of the femur. Different curvatures of the femur neck and various spatial dimensions of the region intertrochanterica can be considered to a sufficient degree to construct a suitable prosthesis.

In addition, the laminar shape of the endoprostheses according to the invention provides the opportunity for manufacturing individual prostheses according to an X-ray template, with the respective lateral plates being cut to conform to the shape of the bone according to the X-ray templates. Additionally, it is possible to individually assemble the endoprostheses in the manner of a modular system.

The respective peripheral edges of the thin plates, i.e. those facing away from the collar of the prosthesis according to the invention, are given a cutting edge configuration which results in extreme simplification of surgery and permits almost complete retention of the natural bone substance. The thin plates are preferably made of titanium sheet metal which may be provided with known biocompatible surface configurations or coatings.

The present disclosure relates to the subject matter disclosed in German Patent Application Nos. G 87 08 501.1 of June 12, 1987 and P 38 02 239.7-35 of Jan. 22, 1988, the entire specifications of which are incorporated herein by reference.

It will be understood that the above description of the present invention is susceptible to various modifications, changes and adaptations, and the same are intended to be comprehended within the meaning and range of equivalents of the appended claims.

What is claimed is:

1. A prosthesis for implanting into a prepared first bone, comprising:
    a plateau having upper and lower surfaces, at least one bearing member configured to receive cooperating condyles of a second bone, said bearing member being disposed on said upper surface of the plateau;
    a U-shaped anchoring element connected to said lower surface of the plateau, said U-shaped anchoring element including two elongated side plates extending outwardly and generally transversely to said lower surface wherein each of said side plates having bottom, front and rear edges; and
    a connecting plate spaced a predetermined distance from said lower surface and extending between and connecting said side plates, said connecting plate and said side plates having means for cutting into the first bone upon insertion of the prosthesis therein.

2. A prosthesis as claimed in claim 1, wherein said connecting plate is a first connecting plate and said two plates have respective rear edges, and further comprising a second connecting plate connecting said rear edges of said two plates.

3. A prosthesis as claimed in claim 2, wherein said second connecting plate has a plurality of perforations for permitting bone growth into said plurality of perforations and between said two plates.

4. A prosthesis as claimed in claim 2, wherein said second connecting plate is additionally connected to said lower side of said plateau.

5. A prosthesis as claimed in claim 1, wherein said two plates are substantially parallel and spaced apart a predetermined distance from each other.

6. A prosthesis as claimed in claim 1, wherein said front edge of said connecting plate has a concave curved shape.

7. A prosthesis as claimed in claim 6, wherein said front edge of said connecting plate is continuous with the front edges of said two plates.

* * * * *